United States Patent [19]

Ser et al.

[11] 4,337,241

[45] Jun. 29, 1982

[54] EMULSIONS OF THE WATER-IN-OIL OR OIL-IN-WATER TYPE AND COSMETIC PRODUCTS USING THESE EMULSIONS

[75] Inventors: Jean-Claude Ser, Beynes; Arlette Zabotto, Paris; Christian Zaffran, Elancourt; Constantin Koulbanis, Paris, all of France

[73] Assignee: L'Oreal S.A., Paris, France

[21] Appl. No.: 878,912

[22] Filed: Feb. 17, 1978

[30] Foreign Application Priority Data

Feb. 23, 1977 [FR] France .................................. 77 05258

[51] Int. Cl.³ ........................ A61K 7/42; A61K 7/021; A61K 31/00
[52] U.S. Cl. ............................ 424/59; 424/DIG. 5; 424/63; 424/168; 424/174
[58] Field of Search .................... 424/63, 59, 168, 174

[56] References Cited

U.S. PATENT DOCUMENTS

| | | | |
|---|---|---|---|
| 3,660,566 | 5/1972 | Vinson et al. | 424/359 |
| 3,926,840 | 12/1975 | Wendler | 424/168 X |
| 4,035,513 | 7/1977 | Kumano | 424/168 X |

FOREIGN PATENT DOCUMENTS 47-03330  1/1972  Japan .................................. 424/365

OTHER PUBLICATIONS

Thewlis Amer. Perfumer & Cosmetics, 8/1971, vol. 86, pp. 39 to 42 & 44.
Burnett Amer. Perf. & Cosmetics, 10/1963, pp. 69 to 72.

*Primary Examiner*—Dale R. Ore

[57] ABSTRACT

Stable emulsions are provided which can be either in the form of "water-in-oil" or "oil-in-water" emulsions and are obtained using a mixture of lanolin acid and at least one natural basic α-amino acid, the proportions in the mixture determining the form of the emulsion.

21 Claims, No Drawings

EMULSIONS OF THE WATER-IN-OIL OR OIL-IN-WATER TYPE AND COSMETIC PRODUCTS USING THESE EMULSIONS

The present invention relates to new emulsions of the "water-in-oil" or "oil-in-water" type which can be used, in particular, in the field of cosmetics or as a pharmaceutical excipient.

It is known that emulsions can exist in two forms, either in the "water-in-oil" form or in the "oil-in-water" form, the form of the emulsion generally being determined by the emulsifier used.

With the aim of obtaining either "water-in-oil" emulsions or "oil-in-water" emulsions, various emulsifiers have already been proposed, but these are specific. In other words, an emulsifier which leads to the formation of a "water-in-oil" emulsion cannot be used to form an "oil-in-water" emulsion, and vice versa.

Thus, soaps of lanolin acid (a mixture of fatty acids) with monovalent metals lead more particularly to "oil-in-water" emulsions, whereas lanolin acid soaps of di- and tri-valent metals preferentially lead to emulsions of the "water-in-oil" type.

Other types of specific emulsifiers have been proposed; mixtures of an oxypropyleneated/polyglycerolated alcohol and magnesium isostearate, succinic esters of a polyoxyalkyleneated fatty alcohol and oxypropyleneated/oxyethyleneated alcohols may be particularly mentioned for the production of emulsions of the "water-in-oil" type. Substances such as lanolin, polycyclic alcohols, such as sterols, and high molecular weight aliphatic alcohols, most of which are constituents of waxes, are known for use as emulsifiers for emulsions of the "water-in-oil" type.

With the aim of facilitating the work of cosmetic scientists, it is important to perfect emulsifiers which make it possible to obtain either "water-in-oil" emulsions or "oil-in-water" emulsions.

We have found, according to the present invention, completely surprisingly, that this result can be obtained by using certain mixtures of lanolin acid and at least one natural basic α-amino-acid as the emulsifier.

In fact, we have found that simply by varying the porportions either of the lanolin acid or of the natural basic α-amino-acid, it is possible to produce either emulsions of the "water-in-oil" type or emulsions of the "oil-in-water" type under excellent conditions.

Furthermore, we have found, surprisingly, that the use of an emulsifier of this kind makes it possible to obtain emulsions having various pH values, which could only be achieved hitherto by using a well-defined type of emulsifier for each desired pH.

Thus, according to this invention, it is possible to obtain excellent emulsions from solutions which are buffered at pH values generally from 2.9 to 8.9. A result of this kind cannot be obtained with conventional emulsifiers because the emulsion is found to break immediately on acidifying with, for example, hydrochloric acid.

Again, we have found that the emulsions of the present invention exhibit excellent fluidity, especially when the emulsifer is used together with lanolin alcohol or hydrogenated lanolin.

The emulsions according to the invention furthermore exhibit excellent stability, which makes it possible to avoid the use of stabilisers such as, for example, wax or vaseline.

The present invention accordingly provides a stable emulsion of the "water-in-oil" or "oil-in-water" type which comprises a water phase, an oil phase and an emulsifier which is a mixture of lanolin acid and at least one natural basic α-amino acid.

"Natural basic α-amino-acid", as used herein, means an α-amino-acid which is known under the name of a hexone base, and especially arginine, histidine and lysine.

It is known that lanolin acid (or lanolic acid) is obtained by hydrolysing lanolin (or lanolin esters) which is composed of about 94% of fatty acid esters (see, for example, A. W. Weitkamp, J. Am. Chem Soc. 67, 447 (1945)).

Lanolin acid itself is in fact a rather complex mixture of fatty acids which more particularly include aliphatic acids, which may or may not be substituted, and hydroxylic acids. The analyses which have been carried out hitherto have enumerated about 36 different fatty acids. Depending on the origin of the lanolin acid and on the method of hydrolysis, the lanolin acid can generally have a mean molecular weight of between about 350 and about 480. In general, lanolin acid occurs in the form of a compact or granular wax having a pale yellow to light brown colour.

Lanolin acids which can be used in the production of the emulsions according to the invention include those known under the tradenames "AMERLATE WFA", sold by Messrs. AMERCHOL, and "LANACID", sold by Messrs. MALMSTROM, as well as the "Acides Lanoliques" ("Lanolin Acids"), sold by Messrs. CRODA.

According to this invention, emulsions of the "water-in-oil" type are generally obtained by using weight ratios of lanolin acid/natural basic α-amino-acid of 98:2 to 82:18, and preferably 92:8 to 85:15.

According to this invention, emulsions of the "oil-in-water" type are generally obtained by using weight ratios of lanolin acid/natural basic α-amino-acid of 80:12 to 60:40, and preferably 78:22 to 72:28.

Ratios of 82:18 to 80:20 generally lead to intermediate emulsions. It has therefore been found that, only by varying the ratios of the lanolin acid to the natural basic α-amino-acid, it is possible to obtain either emulsions of the "water-in-oil" type or emulsions of the "oil-in-water" type.

The emulsifier is generally present in the emulsion at a concentration of 6 to 20%, and preferably 10 to 18%, by weight.

According to a particular embodiment, the emulsifier is used together with lanolin alcohol and/or hydrogenated lanolin in an amount from, say, 6 to 12%, and preferably 8 to 10%, by weight relative to the total weight of the emulsion. It is thereby possible to obtain emulsions having excellent fluidity and very good stability.

"Hydrogenated lanolin" are used herein to mean the mixture of alcohols which are obtained by the catalytic hydrogenation of lanolin which is essentially composed of esters. Its preparation consists in initially hydrogenolysing lanolin (or lanolin esters) to give a mixture of free acids and alcohols, and then in catalytically reducing the free acids to give the corresponding alcohols.

Its preparation can be represented schematically in the following manner:

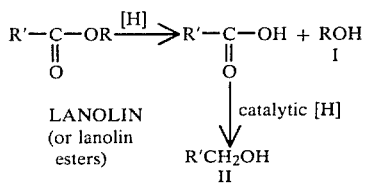

the hydrogenated lanolin being the mixture of the alcohols I and II above.

"Lanolin alcohol" is used herein to mean the alcohols obtained by hydrolysing the esters which constitute lanolin. As indicated above the acid resulting is called lanolin acid. According to recent analyses, lanolin alcohol is composed of about 33 different alcohols which belong to three separate classes, namely aliphatic alcohols, triterpenoic alcohols and sterols.

Hydrogenated lanolin or lanolin alcohol should preferably have a hydroxyl number of 130 to 170, a drop point of 34° to 70° C., and a peroxide number which is less than or equal to 10.

As hydrogenated lanolins, those known under the tradenames "HYDROLAN", sold by Messrs. MILLSMASTER ONYX and having a melting point of 48°–53° C., "HYDROXYOL", sold by Messrs. MALMSTROM, and "SUPER-SAT", sold by Messrs. RITA Chemical and having a melting point of 48°–50° C., are suitably used.

As lanolin alcohols, those known under the tradenames "HARTOLAN" and "SUPER HARTOLAN", sold by Messrs. CRODA, and "LANOCERINA", sold by Messrs. ESPERIS, are suitably used.

In general, the emulsions according to the invention comprise a water phase amounting to say, 20 to 70% by weight, and preferably 25 to 60% by weight, and an oily phase amounting to, say, 20 to 75% by weight, and preferably 30 to 55% by weight, relative to the total weight of the emulsion.

A large variety of products can be employed to form the "oil" phase of the emulsions according to the invention, such as hydrocarbon oils, such as paraffin oil, Purcellin oil and perhydrosqualene, and solutions of microcrystalline wax in these oils, animal or vegetable oils, such as sweet-almond oil, avocado oil, callophylum oil, lanolin, castor oil, caballine oil, lard oil and olive oil, mineral oils having an initial distillation temperature at atmospheric pressure of about 250° C. and a final distillation temperature of the order of 410° C., and saturated esters such as isopropyl palmitate, alkyl myristates such as isopropyl, butyl and cetyl myristates, hexadecyl stearate, ethyl palmitate, the triglycerides of octanoic and decanoic acids and cetyl ricinoleate.

If desired, silicone oils which are soluble in the other oils, such as dimethylpolysiloxane, methylphenylpolysiloxane and silicone/glycol copolymer, can be added to the "oil" phase.

Waxes such as carnauba wax, Candelilla wax, beeswax, microcrystalline wax and ozokerite can also be used in order to assist retention of the oils.

The present invention also provides cosmetic compositions which are obtained from the emulsions of this invention. These cosmetic compositions can exist in various forms.

Emulsions of the "water-in-oil" type make it possible to produce compositions which exist in the form of moisturising creams such as sun creams, face creams, body creams or hand creams, or in the form of moisturising rouges or make-up foundations. These compositions based on emulsions of the "water-in-oil" type can also exist in the form of moisturising sticks for the face, body and lips, or for eye make-up.

Emulsions of the "oil-in-water" type also make it possible to produce compositions which exist in the form of creams, or preferably in the form of milks, for the care or cleansing of the face, body or hands. These compositions can also exist in the form of make-up foundations.

The cosmetic compositions according to the invention can contain the ingredients which are generally used in cosmetics, in particular dyestuffs, pigments, perfumes and preservatives such as methyl parahydroxybenzoate or propyl parahydroxybenzoate, the latter making it possible to increase the stability and the keeping properties of the emulsion.

The cosmetic compositions according to the invention have an excellent affinity for the skin and, by virtue of the nature of the emulsifier used, these emulsions make it possible to apply, to the skin, substances, namely natural $\alpha$-amino-acids, which are present in the epidermis in more or less complexed forms.

As indicated above, the emulsions according to the invention can also be used in the production of pharmaceutical excipients such as creams, ointments and balms.

The present invention also provides a process for the preparation of the emulsions according to the invention, this process being essentially characterised in that, in a first stage, the lanolin acid is dissolved in the "oil" phase at a temperature of about 80° C., whilst stirring, in that, in a second stage, the "water" phase containing the natural basic $\alpha$-amino-acid is added at a temperature of about 80° C. and in that, finally, emulsification is carried out by rapid stirring using a stirrer or a turbine; the emulsion can then be allowed to cool to ambient temperature, whilst stirring more slowly. When the operation is complete, the emulsion can be fined, if desired, by passing it through a roll mill.

The following Examples further illustrate the present invention.

EXAMPLE 1

A "water-in-oil" emulsion, which can be used in cosmetics or as a pharmaceutical excipient, is prepared according to the invention by mixing the following ingredients:

| | |
|---|---|
| Lanolin acid | 7.2 g |
| Lysine | 0.8 g |
| Lanolin alcohol (LANOCERINA) | 8 g |
| Paraffin oil | 34 g |
| Water, q.s.p. | 100 g |

This emulsion is prepared by melting the lanolin acid in the paraffin oil at about 80° C. and then by adding the water part which contains the lysine and has been heated to about 80° C.

Emulsification is then carried out by stirring using a turbine, and the emulsion is then allowed to return to ambient temperature and is fined, if desired, by passing it through a roll mill.

EXAMPLE 2

An "oil-in-water" emulsion, which can be used in cosmetics or as a pharmaceutical excipient, is prepared according to the invention by mixing the following ingredients:

| Lanolin acid | 8 g |
|---|---|
| Lysine | 2 g |
| Paraffin oil | 30 g |
| Water, q.s.p. | 100 g |

EXAMPLE 3

A "water-in-oil" emulsion, which can be used in cosmetics or as a pharmaceutical excipient, is prepared according to the invention by mixing the following ingredients:

| Lanolin acid | 14.4 g |
|---|---|
| Histidine | 1.6 g |
| Paraffin oil | 34 g |
| Water, q.s.p. | 100 g |

EXAMPLE 4

An "oil-in-water" emulsion, which can be used in cosmetics or as a pharmaceutical excipient, is prepared according to the invention by mixing the following ingredients:

| Lanolin acid | 7 g |
|---|---|
| Histidine | 3 g |
| Paraffin oil | 30 g |
| Water, q.s.p. | 100 g |

EXAMPLE 5

An "oil-in-water" emulsion, which can be used in cosmetics or as a pharmaceutical excipient, is prepared according to the invention by mixing the following ingredients:

| Lanolin acid | 4.5 g |
|---|---|
| Arginine | 1.5 g |
| Hydrogenated lanolin | 6 g |
| Caprylate ester | 7 g |
| Water, q.s.p. | 100 g |

EXAMPLE 6

A "water-in-oil" emulsion, in the form of a cream which can be used in cosmetics or as a pharmaceutical excipient, is prepared according to the invention by mixing the following ingredients:

| Lanolin acid | 7.2 g |
|---|---|
| Arginine | 0.8 g |
| Hydrogenated lanolin | 8 g |
| Isopropyl palmitate | 8 g |
| Water, q.s.p. | 100 g |

The emulsions according to Examples 2 to 6 are obtained in accordance with the same method of operation as that described in Example 1.

EXAMPLE 7

A "water-in-oil" emulsion, in the form of a cream, is prepared according to the invention by mixing the following ingredients:

| Lanolin acid | 13.5 g |
|---|---|
| Arginine | 1.5 g |
| Hydrogenated lanolin | 15.0 g |
| Paraffin oil | 35.0 g |
| Preservative | 0.15 g |
| Perfume | 0.1 g |
| Water, q.s.p. | 100 g |

This emulsion is prepared by melting the lanolin acid in the hydrogenated lanolin and the paraffin oil at about 80° C., and then by adding the water part which contains the arginine and has been heated to about 80° C.

Emulsification is then carried out by stirring using a turbine, and the emulsion is then allowed to return to ambient temperature and the preservative and perfume are added.

On acidifying with HCl, for example, to pH 3, no breaking of the emulsion is found.

EXAMPLE 8

An "oil-in-water" emulsion, in the form of a fluid cream, is prepared according to the invention by mixing the following ingredients:

| Lanolin acid | 7.8 g |
|---|---|
| Arginine | 2.2 g |
| Paraffin oil | 32.0 g |
| Preservative | 0.10 g |
| Perfume | 0.2 g |
| Water, q.s.p. | 100 g |

This emulsion is produced in accordance with the same method of operation as that described in Example 7 above.

EXAMPLE 9

An "oil-in-water" emulsion, in the form of a makeup foundation, is prepared according to the invention by mixing the following ingredients:

| Lanolin acid | 7.5 g |
|---|---|
| Arginine | 2.5 g |
| Paraffin oil | 30 g |
| Preservative | 0.1 g |
| Perfume | 0.2 g |
| Dyestuffs and pigments | 10 g |
| Water, q.s.p. | 100 g |

This emulsion in the form of a make-up foundation is produced in accordance with the same method of operation as that described in Example 7; however, the dyestuffs and pigments are introduced during emulsification.

EXAMPLE 10

A "water-in-oil" emulsion, in the form of a make-up foundation, is prepared according to the invention by mixing the following ingredients:

| Lanolin acid | 14.25 g |
|---|---|
| Arginine | 0.75 g |
| Paraffin oil | 30 g |
| Preservative | 0.15 g |
| Perfume | 0.1 g |
| Dyestuffs and pigments | 10 g |
| Water, q.s.p. | 100 g |

This emulsion is prepared in the same manner as the emulsion described in Example 9.

Of course, the embodiments of the invention which have been described have only been given by way of indication and they will be able to undergo any desirable modification, without thereby going outside the scope of the invention.

It will be understood that the emulsions according to the invention can also be used in fields other than those of cosmetics and of excipients for pharmaceutical products.

We claim:

1. A stable emulsion of the "water-in-oil" or "oil-in-water" type comprising an aqueous phase, an oil phase and an emulsifier which is a mixture of lanolin acid and at least one natural basic α-amino-acid.

2. A stable emulsion of the "water-in-oil" or "oil-in-water" type comprising an aqueous phase, an oil phase and an emulsifier, said emulsifier being a mixture of lanolin acid and at least one natural basic α-amino-acid selected from the group consisting of arginine, histidine and lysine, and said emulsifier being present in an amount from 6 to 20% by weight of the emulsion.

3. An emulsion according to claim 1 in which the natural basic α-amino-acid is selected from arginine, histidine and lysine.

4. An emulsion according to claim 1, in which the lanolin acid has a mean molecular weight of about 380 to about 480.

5. A "water-in-oil" emulsion according to claim 1, in which the weight ratio of lanolin acid to natural basic α-amino-acid is from 98:2 to 82:18.

6. An emulsion according to claim 5, in which the said weight ratio is from 92:8 to 85:15.

7. An "oil-in-water" emulsion according to claim 1, in which the weight ratio of lanolin acid to natural basic α-amino-acid is from 80:20 to 60:40.

8. An emulsion according to claim 7 in which the said weight ratio is from 78:22 to 72:28.

9. An emulsion according to claim 1 in which the emulsifier is present in an amount from 6 to 20% by weight relative to the total weight of the emulsion.

10. An emulsion according to claim 9 in which the emulsifier is present in an amount from 10 to 18% by weight.

11. An emulsion according to claim 1 which also contains an adjuvant selected from lanolin alcohol and hydrogenated lanolin in an amount from 6 to 12% by weight.

12. An emulsion according to claim 11 in which the said adjuvant is present in an amount from 8 to 10% by weight.

13. An emulsion according to claim 1 in which the water phase is present in an amount from 20 to 70% by weight.

14. An emulsion according to claim 13 in which the water phase is present in an amount from 25 to 60% by weight.

15. An emulsion according to claim 1 in which the oil phase is present in an amount from 20 to 75% by weight.

16. An emulsion according to claim 15 in which the oil phase is present in an amount from 20 to 55% by weight.

17. An emulsion according to claim 1 in which the oil phase of the emulsion comprises at least one oil taken from the group consisting of paraffin oil, Purcellin oil, perhydrosqualene, or a solution of microcrystalline wax therein, sweet-almond oil, avocado oil, callophylum oil, lanolin, castor oil, caballine oil, lard oil, olive oil, a mineral oil, having an initial distillation temperature at atmospheric pressure of about 250° C. and a final distillation temperature of about 410° C., isopropyl palmitate, isopropyl, butyl or cetyl myristate, hexadecyl stearate, ethyl palmitate, a triglyceride of octanoic or decanoic acid and cetyl ricinoleate.

18. An emulsion according to claim 1, in which the emulsion contains a cosmetic ingredient selected from the group consisting of a dyestuff, a pigment, a perfume, a preservative and mixtures thereof.

19. An emulsion according to claim 1 in which the oil phase contains a wax selected from the group consisting of carnauba wax, Candelilla wax, beeswax, microcrystalline wax and ozokerite.

20. Process for the preparation of an emulsion as defined in claim 1 which comprises first dissolving the lanolin acid in the oil phase at a temperature of about 80° C., whilst stirring, and second adding the water phase containing the natural basic α-amino acid at a temperature of about 80° C. and then stirring the mixture sufficiently to cause emulsification.

21. Process according to claim 20, in which the emulsion is fined by passing it through a roll mill.

* * * * *